United States Patent [19]
Wolf et al.

[11] Patent Number: 5,179,003
[45] Date of Patent: Jan. 12, 1993

[54] PROCESS FOR THE PRODUCTION OF PROTEINS OR PROTEIN-CONTAINING GENE PRODUCTS

[75] Inventors: Dieter H. Wolf, Gundelfingen; Erhard Kopetzki, Tutzing; Günther Schumacher, Bernried, all of Fed. Rep. of Germany

[73] Assignee: Boehringer Mannheim GmbH, Mannheim-Waldhof, Fed. Rep. of Germany

[21] Appl. No.: 293,502

[22] Filed: Jan. 4, 1989

[30] Foreign Application Priority Data

Jan. 5, 1988 [DE] Fed. Rep. of Germany ....... 3800134
Feb. 17, 1988 [DE] Fed. Rep. of Germany ....... 3804890

[51] Int. Cl.$^5$ .................. C12P 21/00; C12P 21/02; C12N 1/16; C12N 1/19
[52] U.S. Cl. .................. 435/69.1; 435/252.3; 435/172.1; 435/255; 435/740; 435/37; 435/61; 435/69
[58] Field of Search .............. 435/69.1–69.6, 435/172.1–172.3, 320.1, 252.3

[56] References Cited

U.S. PATENT DOCUMENTS

| | | | |
|---|---|---|---|
| 4,816,397 | 3/1989 | Boss et al. | 435/68 |
| 4,855,231 | 8/1989 | Stroman et al. | 435/68 |
| 4,902,620 | 2/1990 | Bard et al. | 435/172.3 |

FOREIGN PATENT DOCUMENTS 03949  9/1985  PCT Int'l Appl. .

OTHER PUBLICATIONS

Segal, et al., 1976, in *Metabolic Conversions of Enzymes, 4th International Symposium*, Shmwel, S., Ed., Springer-Verlag pp. 185–190.
Libby, P., et al., 1981, Journal of Cellular Physiology 107: 185–194.
Mayor, J. R., et al., 1986 Biomedica et Biochemica Acta 45 (11–12): 1591–1602.
Tessitore, L., et al., 1987, Archives of Biochemistry and Biophysics 255 (2): 372–384.
Jahoor, F., et al., 1987, Kidney International vol. 32, Suppl. 22, pp. S–81–S–93.
Bohley, P., et al., 1979 in *Biological Functions of Proteinases*, Hulzer, H., et al., Eds., 30th Mosbach Colloquium, Springer-Verlag, at pp. 17–34.
Dean, R. T., 1979, in *Biological Functions of Proteinases*, Holzer, H., et al, Eds., 30th Mosbach Colloquium, Springer-Verlag, at pp. 49–54.
Wolf, D. H., et al., 1979, in *Biological Functions of Proteinases*, Holzer, H., et al., Eds., 30th Mosbach Colloquium, Springer-Verlag at pp. 55–72.
Bröker, M., et al., 1991, Applied Microbiology and Biotechnology, 34: 756–764.
Strathern, J. N., et al, 1982, *The Molecular Biology of the Yeast Saccharomyces*, Cold Spring Harbor Laboratory Press, at 377–381.
Häggström, M. H., et al., 1984, Applied Biochemistry and Biotechnology 9:475–481.
Kopetzki, E., et al., 1989, Yeast, 5: 11–24.
Jones, E. W., 1991, The Journal of Biological Chemistry, 256(3):7963–7966.
Achstetter, T., et al, 1984, Journal of Biological Chemistry, 259(21): 13334–13343.
Emter, O., et al., 1984, FEBS Letters, 166(2):321–325.
Achstetter, T., et al., 1985, Journal of Biological Chemistry, 260(8): 4585–4590.
Kistler, M., et al., 1986, Mutation Research, 173(2): 117–120, (abstract).
Korch, C. T., and R. Snow, 1973, Genetics, 74(2): 287–305, (abstract).
Ammerer, G., et al., 1986, Molecular and Cellular Biology, 6(7): 2490–2499.
Woolford, C. A., et al., 1986, Molecular and Cellular Biology, 6(7): 2500–2510.
Nanmorski, L., and E. C. Friedberg, 1983, Gene, 22: 203–209.
Achstetter, et al., Yeast 1: 139–157 (1985).
Mechler, et al., EMBO J 6(7): 2157–2163 (1987).
Search Report for EP/89/10 0104.

*Primary Examiner*—Robert A. Wax
*Assistant Examiner*—William W. Moore
*Attorney, Agent, or Firm*—Felfe & Lynch

[57] ABSTRACT

The present invention provides a process for the production of proteins or protein-containing gene products by transformation of eukaryotic host cells with a recombinant DNA molecule containing the gene for the desired protein, culturing the cells and isolating the gene product after expression, wherein, as host cells, there is used a yeast strain which is deficient in proteases A and B.

11 Claims, No Drawings

PROCESS FOR THE PRODUCTION OF PROTEINS OR PROTEIN-CONTAINING GENE PRODUCTS

The present invention is concerned with a process for the preparation of proteins or protein-containing gene products by gene technology by the transformation of eukaryotic host cells with a recombinant DNA molecule containing the gene for the desired protein, culturing the cells and isolating the gene product in known manner.

The determination of clinical-chemical parameters today takes place to a large extent by enzymatic methods. The enzymes used for the preparation of the reagents needed therefor are obtained from various sources of plant or animal origin or from micro-organisms.

For the preparation of enzymes and of other proteins, micro-organisms are of increasing importance since only these can be made available in practically any desired amounts by cultivation and thus make possible the isolation of comparatively large amounts of proteins.

As in known, yeasts, for example, *Saccharomyces cerevisiae* are important since besides homologous expression of proteins, heterologous expression of eukaryotic proteins can take place in these organisms as well, for example, expression of those heterologous proteins which are of therapeutic importance. On the other hand, in *Escherichia coli*, which is the most commonly used host organism, many heterologously expressed proteins differ from their natural counterparts expressed in a homologous system and are biologically inactive or are obtained as insoluble inactive protein aggregates, which are called "refractile bodies". Many eukaryotic proteins which are expressed inactively in *Escherichia coli* are soluble in *S. cerevisiae* and are formed actively (Biotechnology and Genetic Engineering Reviews, 3, 377-416/1985). This may, amongst other things, be due to the fact that yeasts are capable of secretion via the typical eukaryotic post-translational modification systems, for example "protein folding", protein maturing, glycosylation and acetylation, are capable of secretion and disulphide bond formation in polypeptides and proteins. Furthermore, yeasts are not pathogenic and, in contrast to *Escherichia coli*, are free from toxins and pyrogenic cell wall components.

Yeast is one of the oldest culture organisms known to man. It was and still is mainly used for alcoholic fermentation (wine, beer and the like) and as a "bakers' aid" for the production of dough products. In addition, yeast is of industrial importance as an economic raw material source for the isolation of low molecular weight substances, for example NAD, ATP and glutathione, and of high molecular weight substances, for example DNA, RNA and, in particular, enzymes, such as alcohol dehydrogenase, aldehyde dehydrogenase, acetyl-CoA-synthetase, α-glucosidase, glyceraldehyde-3-phosphate dehydrogenase, glucose-6-phosphate dehydrogenase and hexokinase. Yeast is easy to culture and, because of long years of experience, is simple to culture on an industrial scale. Yeast, which belongs to the lower eukaryotes, possesses the typical characteristics of a eukaryote but, nevertheless, is easily accessible to genetic investigations and genetic manipulations, for which reason it is especially suitable as a host organism having regard to recombinant DNA technology, i.e. for the homologous and heterologous expression of biologically active polypeptides and proteins.

However, in the case of the expression of proteins in yeasts, in many cases the amount of protein formed is not satisfactory. It is frequently found that, after reaching the early stationary growth phase, the specific activity of a desired protein again decreases in the course of the stationary growth phase, although the biomass formed of the micro-organisms still increases. This is, inter alia, to be attributed to a proteolytic attack of host-specific proteases on the synthesized proteins.

Therefore, it is an object of the present invention to provide a process for the preparation of proteins by gene technology with which proteins are also formed and are stably accumulated in the stationary growth phase and thus the yield of the fermentation process can be increased.

According to the present invention, there is provided a process for the production of proteins or protein-containing gene products by transformation of eukaryotic host cells with a recombinant DNA molecule containing the gene for the desired protein, culturing the cells and isolating the gene product after expression, wherein, as host cells, there is used a yeast strain which is deficient in proteases A and B.

The yeast strain used is preferably also deficient in protease D.

In a preferred embodiment of the present invention, a yeast strain is used which, in addition to the deficiency in proteases A, B and possibly D, is also deficient in at least one of the carboxypeptidases Y and S.

The designation of the proteases and carboxypeptidases in the description of the present invention corresponds to the designation used in Yeast, 1, 139-154/1985.

Due to the use of these protease-deficient yeast strains in the process according to the present invention, it is possible to produce proteins or protein-containing gene products in yeast in increased yields without, in the case of extremely long culturing times or in the case of the subsequent isolation according to known methods, a proteolytic attack also taking place and thus an inactivation of the proteins.

In an especially preferred embodiment of the present invention, as host cell there is used the yeast strain ABYSD-11 (DSM 4322). This host strain is deficient with regard to the proteases A, B and D and with regard to the carboxypeptidases Y and S. In addition, it is auxotrophic for the biosynthesis of adenine, histidine and lysine.

Auxotrophy means the inability of micro-organisms (mostly mutants of bacteria and yeasts) to synthesise certain growth factors, for example amino acids, from simple precursors. In contrast to the corresponding wild type strains, auxotrophic mutants thereby do not grow on so-called minimal media. On the contrary, they require a complete medium or minimal medium supplemented the components necessary for growth which they cannot synthesize themselves. Micro-organisms can be auxotrophic for one but also for several growth factors (E.-L. Winnacker, Gene and Klone, 1985, pub. Verlag Chemie, Appendix C).

In a further preferred embodiment of the present invention, the protease-deficient yeast strain is crossed with another auxotrophic and/or chemically-sensitive yeast strain, after sporulation, by selecting via the auxotrophy and/or sensitivity, from the hybrid strain there is isolated a yeast strain which is at least deficient in protease A and B and displays at least one of the auxotrophies and/or chemical sensitivities of the parent strains and this hybrid strain is used as host cells.

By chemical sensitivity is to be understood the inability of a micro-organism to grow in a medium which contains certain chemicals, for example methotrexate, chloramphenicol or the gentamycin derivative G418. Only after transformation of the micro-organism with a recombinant DNA which contains a gene which imparts to the micro-organism resistance to these chemicals (dehydrofolate reductase, DHFR; chloramphenicol acetyl transferase, CAT; transposon Tn601- encoded aminoglycoside phosphotransferase and the like) can the micro-organism grow in the medium. The crossing and sporulation can be carried out, for example, analogously to Sherman et al., Methods in Yeast Genetics, Cold Spring Harbor Laboratory, Cold Spring Harbor, N.Y., 1984. In an especially preferred embodiment of the present invention, for this purpose the yeast strain ABYSD-11 (DSM 4322) (a pral, prbl, prcl, prdl, cpsl, ade, lys, his 7) is crossed either with the yeast strain TCY2824-1A (α mallS-Δ ura3-52 his 4) (DSM 4317) or DBY 746 (DSM 4316) (α his3-Δ1 leu2-3 leu2-112 ura3-52 trpl-289a). These strains have a defective maltase structural gene, and are auxotrophic for uracil and histidine or are auxotrophic for histidine, leucine, uracil and tryptophan. Strains (segregants) are then preferably isolated which are deficient in proteases A and B and possibly D and in the carboxypeptidases Y and S and, in addition, are auxotrophic for at least one of, e.g. uracil, leucine and maltose utilization or both leucine and tryptophan utilization or, finally, all of the leucine, uracil and histidine auxotrophies of the parent strains.

Therefore, in a further preferred embodiment of the present invention, the recombinant DNA molecule contains, in addition to the gene for the desired protein or protein-containing gene product, one or more genes which complement the auxotrophies and/or chemical sensitivities of the host strain.

By means of the preferred embodiment of the present invention, a simple differentiation of transformed and non-transformed host cells is possible. The presence and expression of genes which complement one or more auxotrophies and/or chemical sensitivities of the host strain thus also makes possible the growth of transformed cells on media which, for example, do not contain an amino acid which the host strain itself cannot synthesize but the gene of which is present on the recombinant DNA molecule. Non-transformed host strains which thus do not have the recombinant DNA molecule and the auxotrophy-complementing gene contained thereon can, on the other hand, not grow in such a medium. In this way, in a simple manner there can be carried out selection of transformed host cells, whereby the danger of a loss of the recombinant DNA which contains the gene for the desired protein during the fermentation is avoided since there is no growth advantage for the non-transformed cells.

Alternatively, it is also possible to overcome the auxotrophy and/or chemical sensitivity of a host strain by introduction of a further additional recombinant DNA molecule which contains one or more genes which complement the auxotrophies and/or chemical sensitivities of the host cell. Thereby, however, a simple method of selection of the host cells containing the gene for the desired product cannot be carried out.

For the recombinant DNA molecules, there can be used all recombinant DNA molecules with which yeast cells can be transformed and which are capable of expressing a foreign gene. There can thereby be considered not only the extrachromosomal transcription of, for example, a plasmid but it is also possible to introduce the gene for the desired protein via an integration vector or an integrating DNA fragment which, in each case, contains a complete expression cassette (promoter, terminator, regulating sequenes, transcription enhancer, upstream activation site, UAS and the like) into the yeast genome and to express it together with the native yeast proteins. A prerequisite for this is the presence of DNA-sequence homologies on the recombinant DNA molecule and chromosomal yeast sequences. Via such homologous regions, an integrating DNA fragment can be introduced into a yeast chromosome by known methods.

Therefore, in a further preferred embodiment of the present invention, the recombinant DNA molecule is either a plasmid or an integration vector or an integrating DNA fragment. As plasmids, there are thereby again especially preferred yeast plasmids which occur in the cells in high copy number. Such yeast plasmids are, for example, hybrid yeast/*Escherichia coli* vectors ("shuttle vectors") which are referred to as YRp, YEp, YIp and YCp. In turn, only the YEp and YRp plasmids occur in the cells in high copy number. These because of the presence of sequences which make possible an independent replication of the plasmids, are independent of the replication of the yeast chromosome and are normally present in copy numbers of 5 to 40 per cell. Expression by YIp plasmids can only be achieved by integration of the YIp plasmids into the yeast genome. They are, therefore, examples of integration vectors. YIp plasmids display a ten times lower transformation rate but a significantly greater plasmid stability in comparison with YRp and YEp plasmids. Without selection pressure, YRp and YEp plasmids can be lost in the case of cell multiplication (Nature, 305, 391-397/1983). However, such a selection pressure exists in the case of the preferred embodiment of the present invention in which the fermentation of auxotrophic or chemical-sensitive host strains is carried out in minimal media or in media which contain a particular chemical for which the host strain is sensitive and the recombinant DNA additionally has one or more genes which complement the auxotrophy or sensitivity.

The present invention makes possible the expression of homologous or heterologous proteins or protein-containing gene products in high yield and in a form which cannot be attacked proteolytically, whereby selection of transformed cells and thereby also an increase of the yield of the desired gene product can be carried out in a simple way. Also after cell lysis and during the further procedure for obtaining the gene product according to known methods, because of the protease deficiency of the host cells, no proteolytic attack takes place on the product formed.

In a preferred embodiment of the present invention, the protein α-glucosidase PI is produced (see also the following Example 4).

The following Examples are given for the purpose of illustrating the present invention:

EXAMPLE 1

For the isolation of the Saccharomyces strains ABYSMAL 81 and ABYSDMAL 81, the haploid *Saccharomyces cerevisiae* strain ABYSD-11 (a pral prbl prcl prdl cpsl, ade lys his7) (DSM 4322), which is deficient in proteases A, B and D and in carboxypeptidases Y and S and additionally is auxotrophic for in adenine, histidine and lysine biosynthesis, is crossed with the *Saccharomyces carlsbergensis* strain, TCY2824-1A, (α mallS-Δ ura3-52 his4) (DSM 4317), which is characterised by a defective α-glucosidase structural gene and is auxotrophic for uracil and histidine biosynthesis.

Subsequently, sporulation is carried out and the resultant yeast segregants are tested for their auxotrophies by plating them out on various selection media and by assaying for their protease deficiencies by determination of the protease activities in cell lysates. The strains ABYSDMAL81 (ura3-52 mallS-Δ lys pral prbl prcl prdl cpsl) and ABYSMAL81 (ura3-52 mallS-Δ lys pral prbl prcl cpsl) were identified by:

Detection of the protease deficiencies

The segregants were cultured in 5 ml. YEPD medium (1% yeast extract, 2% peptone, 2% glucose), and the cells were harvested in the late logarithmic to early stationary growth phase, washed twice with water and disrupted with fine glass beads by homogenisation on a whirlmix (MGG, 145, 327–333/1976). Then they were extracted with 1 ml. 20 mMole/liter Tris-HCl (pH 7.0) and the supernatant obtained after centrifugation further worked up as crude extract. For the activation of the proteases, the crude extract was adjusted to pH 5.0 and incubated for 24 hours at 25° C.

Detection of the protease A deficiency (pral)

No hydrolysis by cell extracts of 1.2% acid-denatured haemoglobin (pH 3.0) (Eur. J. Biochem., 42, 621–626/1974) was observed.

0.5 ml. 0.1 mole/liter lactate buffer (pH 3.0) with 1.2% acid-denatured haemoglobin was incubated with 0.1 ml. cell lysate at 25° C. After 30 minutes, the reaction was stopped with 0.5 ml. 10% trichloroacetic acid and, after centrifugation, the trichloroacetic acid soluble products were determined either by absorption measurement at 280 nm or by a modified Folin determination according to McDonald and Chen (Anal. Biochem., 10, 175–177/1965).

For the calculation of the specific activity, there was carried out a protein determination according to Zamenhof (Methods Enzymol., 3, 702/1957).

Protease A deficiency is present when the specific hydrolytic activity of cell lysates towards acid-denatured haemoglobin is reduced to less than 5% in comparison with a wild type strain.

Detection of the protease B deficiency (prbl)

No hydrolysis by cell extracts of 2.4% Azocoll at pH 7 (Eur. J. Biochem., 42, 621–626/1974) was observed.

0.5 ml. of a 2.4% Azocoll suspension in 0.1 mole/liter phosphate buffer (pH 7.0) are incubated with 0.1 ml. of cell lysate with vigorous shaking at 25° C. For the activation of the protease B, the crude extract was mixed with sodium dodecyl sulphate (end concentration 0.25%) before the activity determination.

After 30 minutes, the reaction was stopped by the addition of 0.5 ml. 10% trichloroacetic acid and, after centrifugation, the absorbance of the acid soluble products was measured in the supernatant at 550 nm.

Protease B deficiency is present when the specific hydrolytic activity of cell lysates towards Azocoll is reduced to less than 5% in comparison with a wild type strain.

Detection of the protease D deficiency (prdl)

No hydrolysis by cell extracts of 0.5 mMole/liter Bz-Pro-Phe-Arg-NA (benzoyl-L-prolyl-L-phenylalanyl-L-arginyl-p-nitroanilide) in 50 mMole/liter Tris maleate buffer (pH 7.0) in the presence of aminopeptidase M (J. Biol. Chem., 260, 4585–4590/1985) was observed.

Test principle:

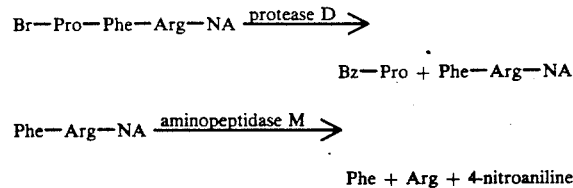

0.03 ml. 0.5 mole/liter Tris maleate buffer (pH 7.0) was mixed with 0.015 ml. 10 mMole/liter Bz-Pro-Phe-Arg-NA (dissolved in dimethyl sulphoxide), 10 μl. (40 μg., 240 MU) aminopeptidase M, 0.145 ml. water and 0.1 ml. of crude extract and the release of 4-nitroaniline was measured at 405 nm against a reagent blank.

Protease D deficiency is present when the specific hydrolytic activity towards Bz-Pro-Phe-Arg-NA is reduced to less than 10% in comparison with a wild type strain.

Detection of the carboxypeptidase Y deficiency (prcl)

No hydrolysis by cell extracts of 0.5 mMole/liter benzoyl-L-tyrosine-4-nitroanilide (pH 7) (Agr. Biol. Chem., 35, 658–666/1971) was observed.

0.1 ml. of crude extract activated with deoxycholate (end concentration 0.5%) was incubated at 25° C. with 1 ml. 0.1 mole/liter phosphate buffer (pH 7.0) and 0.1 ml. 3 mMole/liter benzoyl-L-tyrosine-4-nitroanilide (dissolved in dimethylformamide). After 10 minutes, the reaction was stopped with 1 ml. 1 mMole/liter mercuric chloride and the released p-nitroanilide measured at 410 nm.

Carboxypetidase Y deficiency is present when the specific hydrolytic activity towards benzoyl-L-tyrosine-4-nitroanilide is reduced to less than 5% in comparison with a wild type strain.

Detection of the carboxypeptidase S deficiency (cpsl)

No hydrolysis by cell extracts of Cbz-Gly-Leu (benzyloxycarbonyl-glycyl-L-leucine) at pH 7.4 with subsequent analysis of the released leucine in an L-amino acid oxidase peroxidase test (Eur. J. Biochem., 73, 553–556/1977) was observed.

0.5 ml. of test solution (0.25 mg./ml. L-amino acid oxidase, 0.4 mg./ml. horse radish peroxidase and 0.5 mMole/liter manganese chloride), 0.4 ml. of 27.5 mMole/liter Cbz-Gly-Leu solution (dissolved in 0.2 mole/liter phosphate buffer (pH 7.0)), 0.05 ml. o-dianisidine hydrochloride (2 mg./ml., dissolved in water), 0.05 ml. of 22 mMole/liter phenylmethylsulphonyl fluoride and 0.1 ml. dialyzed cell lysate (dialysis: 0.1M imidazole chloride (pH 5.3); 24 hours at 25° C.) are mixed and the absorbance change determined at 405 nm.

Carboxypeptidase Y deficiency is present when the specific hydrolytic activity towards Cbz-Gly-Leu is reduced to less than 5% in comparison with a wild type strain.

On the basis of the described detections, it was ascertained that the strain ABYSDMAL81 is deficient in proteases A, B and D and carboxypeptidases Y and S and the strain ABYSMAL81 is deficient in proteases A and B and carboxypeptidases Y and S.

Detection of maltose utilisation auxotrophy

No growth on synthetic complete medium I with 0.67% yeast nitrogen base (YNB, salt-vitamin mixture, Difco), 0.5% casamino acids (CAA, protein hydrolysate, Difco), 2% maltose (sole carbon source), 20 mg/liter uracil and 30 mg./liter adenine was observed.

Detection of uracil auxotrophy

No growth on synthetic complete medium II with 0.67% YNB, 0.5% CAA, 2% glucose (sole carbon source) and 30 mg./ml. adenine was observed.

Detection of lysine auxotrophy

No growth on synthetic complete medium II with 20 mg./liter uracil but without lysine (instead of 0.5% CAA, there was used an amino acid mixture without lysine) was observed.

Detection of histidine and adenine prototrophy

Growth on synthetic complete medium II with 20 mg./liter uracil but without adenine and without histidine was observed (instead of 0.5% CAA, there was used an amino acid mixture without histidine).

EXAMPLES 2 AND 3

For the isolation of the Saccharomyces strains ABYSD91 (leu2-3,2-112 trp1-289a pra1 prb1 prd1 prc1 cps1), ABYSD106 (ura3-52 leu2-3,2-112 his pra1 prb1 prd1 prc1 cps1) ABYS91 (leu2-3,2-112 trp1-289a pra1 prb1 prc1 cps1) and ABYS106 (ura-3-52 leu2-3,2-112 his pra1 prb1 prc1 cps1), the *Saccharomyces cerevisiae* strain ABYSD-11 was crossed with the *Saccharomyces carlsbergensis* strain DBY746 (DSM 4316), as described in Example 1. After sporulation, the yeast segregants were tested for their protease deficiencies and auxotrophies.

For ABYS91 and ABYSD91:

Detection of the protease deficiencies

See Example 1

Detection of leucine and tryptophan auxotrophy

No growth on synthetic complete medium II with uracil but without leucine or tryptophan was observed (instead of 0.5% CAA, there was used an amino acid mixture without leucine or tryptophan).

Detection of uracil, adenine, histidine and lysine prototrophy

Growth on synthetic complete medium II without adenine, uracil, histidine and lysine was observed (instead of 0.5% CAA, there was used an amino acid mixture without histidine and lysine).

For ABYS106 and ABYSD106

Detection of the protease deficiencies

See Example 1

Detection of uracil auxotrophy

No growth on synthetic complete medium II was observed.

Detection of leucine and histidine auxotrophy

No growth on synthetic complete medium II with uracil but without leucine or histidine was observed (instead of 0.5% CAA, there was used an amino acid mixture without leucine or histidine).

Detection of adenine, lysine and tryptophan prototrophy

Growth on synthetic complete medium II with uracil but without adenine, lysine and tryptophan was observed (instead of 0.5% CAA, there was used an amino acid mixture without lysine and tryptophane).

EXAMPLE 4

Expression of α-glucosidase PI

The Saccharomyces strain ABYSMAL81 (Example 1) was transformed with the plasmid YEp/5C6b3 (Nature, 275, 104–109/1978).

For the construction of this plasmid, the vector YRp/GLUPI (DSM 4173P) was digested with the restriction endonucleases Ssp I and Hind III, the approximately 3.0 kBp long Ssp I/Hind III fragment was isolated and ligated into the isolated Pvu II/SpH I vector fragment of YEp 24 (Gene, 8, 17–24/1979; Cold Spring Harbor, Symp. Quant. Biol., 43, 77–90/1979; Gene, 29, 113–124/1984; Nature, 286, 860–865/1980), after filling of the overhanging 5'-end of the Hind III restriction cleavage site and removal of the overhanging 3'-end of the Sph I restriction cleavage site with Klenow polymerase. The α-glucosidase PI expression cassette is integrated into the resultant plasmid YEp/S4 in the same orientation as the β-lactamase gene. Thereafter, an approximately 3.1.kBp long Bam HI restriction fragment containing the MAL2-8$^c$p gene was ligated in the single Bam HI site of YEp/S4. For this purpose, the plasmid pRM2 (DSM 4314P) was digested with the restriction endonuclease Sal I, the overhanging 5'-ends filled in with Klenow polymerase, provided with Bam HI linkers (d(CGGGATCCCG)), subsequently cleaved with Bam HI and the 3.1 kBp Bam HI fragment containing the MAL2-8$^c$p gene isolated. The resultant vector construction was designated YEp/5C6b3.

The transformed strain was cultured in YEP medium (1% yeast extract, 2% peptone) with 4% maltose and cultured up to the late logarithmic or stationary growth phase. Subsequently, the biomass was harvested and washed with 10 mMole/liter phosphate buffer (pH 6.8). The cells from 5 ml. YEP-maltose medium (about 0.1 to 0.2 g of yeast, wet weight) were digested by homogenization with a whirlmix (MGG, 145, 327–333/1976).

The determination of the specific α-glucosidase activity took place on the basis of the hydrolysis of p-nitrophenyl-α-D-glucopyranoside (MGG, 151, 95–103/1977) and of the protein determination according to Zamenhof (Methods Enzymol., 3, 702/1957).

In the crude extract obtained in this way, the enzyme was stable for 10 days at 4° C. Furthermore, no changes of the band pattern were found in the SDS gel electrophoresis over this period of time. This shows that the other enzymes and proteins contained in this supernatant are also stable in this yeast strain and are not markedly broken down proteolytically.

In the following Table, the enzymatic stability of the α-glucosidase of bakers' yeast (obtained from Deutsche Hefewerke Nurnberg, DHW) is compared with the stability of recombinant expressed α-glucosidase in protease-deficient α-glucosidase transformants. In bakers' yeast, the specific α-glucosidase activity reaches a maximum in the late logarithmic to early stationary growth phase. In the further course of the cultivation, the specific α-glucosidase activity decreases noticeably (see Table I). In contrast thereto, even after achievement of the stationary growth phase, the α-glucosidase surprisingly accumulates stably in the transformed protease-deficient ma10 strains, the fermentation and working up of the biomass thereby being considerably simplified.

Growth medium: bakers' yeast: 1% yeast extract, 2% peptone and 2% maltose.

ABYSMAL81: synthetic complete medium II.

TABLE

Comparison of the specific α-glucosidase activity in mU/mg protein during the cultivation of bakers' yeast in complete medium supplemented with 2% maltose and the protease-deficient transformant ABYSMAL81-5C6b3 in minimal medium (0.67% yeast nitrogen base, 0.5% casamino acids, 30 mg./l. adenine and 2% glucose).

| | cultivation time | | | | | | | | | |
|---|---|---|---|---|---|---|---|---|---|---|
| | 0 h | | $3^{15}$ h | | $6^{30}$ h | | 24 h | | 36 h | |
| strain | $OD^{600}$ | α-gluc. | $OD^{600}$ | α-gluc. | $OD^{600}$ | α-gluc. | $OD^{600}$ | α-gluc. | $OD^{600}$ | α-gluc. |
| bakers' yeast (DHW-Deutsche Hefewerke Nürnberg) | 3.5 | 1250 | — | — | 15 | 1600 | 25 | 1530 | 25 | 400 |
| | 5 h | | 10 h | | 15 h | | 20 h | | 30 h | | 50 h |
| ABYSMAL81-5C6b3 | 1.4 | 1600 | 9 | 3800 | 17 | 7500 | 21 | 8800 | 25 | 9800 | 26 | 9800 |

EXAMPLE 5

Heterologous expression of a fusion protein, consisting of the N-terminal part of α-glucosidase pI and HIV1 antigens, in protease-deficient yeast strains.

In the α-glucosidase PI expression vector YEp/5C6b3 (see Example 4), the 1.4 KBp long Bgl III fragment, which codes for about 80% of the α-glucosidase PI, was exchanged for an approximately 300 Bp long DNA fragment, which codes for a part of the gp41 membrane protein of the HIV1 retrovirus. For this purpose, an approximately 300 Bp long Rsa I/Hind III fragment (sequence cf. sequence of WMJ-1 from position 1638 to position 1943 from FIG. 1 of Cell, 45, 637–648/1986) was subcloned into the *Escherichia coli* vector pUC18 (M13mp18 and pUC19, sequence in Gene, 33, 103–119/1985) digested with Hinc II and Hind III (construction: pUC18HRH.300). From pUC18HRH.300 was isolated the approximately 320 bp long Bam HI/Hind III fragment and ligated into the approximately 5.2 KBp long pUR278 Bam HI/Hind III vector fragment (sequence in EMBO, 2, 1791–1794/1983) (construction: pUR278HRH.300). The plasmid pUR278HRH.300 was digested with Hind III, the overhanging 5'-ends filled in with "Klenow polymerase" and provided with Bam HI linkers (d(GGGATCCC)). Thereafter, it was subsequently cleaved with Bam HI, the approximately 300 Bp long Bam HI fragment isolated and ligated into the approximately 11 KBp long YEp/5C6b3 Bgl II vector fragment. In the case of correct orientation of the gp41 membrane polypeptide DNA, a fusion protein results consisting of the N-terminus of the α-glucosidase (50 amino acids), 4 construction-caused amino acids at the fusion point, 101 amino acids of the gp41 membrane protein and 3 construction-caused amino acids on the C-terminus with a molecular weight of about 18,500 D. The desired construction was isolated via the expressed fusion protein in the protease-deficient yeast expression strain ABYSMAL81 after transformation and culturing (see below), monitored by SDS gel electrophoresis and Western blot analysis on the basis of immune reactivity with human HIV1 sera. The fusion protein was expressed to about 5% of the total protein and was visible as a dominant band in the SDS polyacrylamide gels after staining with Coomassie blue.

For the expression of a α-gluc.PI-gp41 fusion protein, the transformants were cultured on selective medium (0.67% YNB, 0.5% CAA, 30 mg./liter adenine) supplemented with 2% glucose and 2% maltose. After an induction time of 10 to 20 hours (after glucose consumption), the cells were harvested.

Yeast cell lines have been deposited with the Deutsche Sammlung Von Mikroorganism ("DSM"), Mascheroder Weg 1-B, D-3300 Braunschweig, Germany as follows:

| Yeast line | DMS Designation | Deposit Date |
|---|---|---|
| ABYSD-11 | DSM 4322 | December 17, 1987 |
| TCY 2824-1A | DSM 4317 | December 14, 1987 |
| DBY 746 | DSM 4316 | December 14, 1987. |

What is claimed is:

1. In a process for production of a protein or protein-containing cell product wherein
   yeast cells are transformed with a recombinant DNA molecule containing a gene which codes for said protein or protein contained in said protein-containing cell product, fermenting said cells under conditions favoring expression of said protein or protein in said protein-containing cell product, and
   isolating said protein or protein-containing cell product the improvement consisting of transforming yeast cells of a YEp- or YRp- strain deficient in vacuolar proteases A, B, and one or more proteases selected from the group consisting of carboxypeptidases Y and S to prevent product degradation.

2. Process of claim 1 wherein the improvement further consists of a yeast strain deficient in cytoplasmic protease D.

3. Process of claim 2 wherein said yeast strain is also deficient in at least one of vacuolar proteases carboxypeptidase Y or carboxypeptidase S.

4. Process of claim 3, wherein said yeast strain is ABYSD-11 (DSM 4322).

5. Process for the production of a protein or protein containing cell product comprising crossing a yeast strain deficient in vacuolar proteases A and B with another yeast strain which is auxotrophic or chemically-sensitive, sporulating the product of said crossing, selecting a hybrid yeast strain which is deficient in proteases A and B and is further characterized by at least one auxotrophy or chemical sensitivity of one of the parent strains, transforming said hybrid strain with a recombinant DNA molecule containing a gene which codes for said protein or protein in said protein containing cell product, fermenting said hybrid strain under conditions favoring expression of said protein or said protein in said protein containing cell product and isolating said protein or protein containing cell product.

6. Process of claim 5, wherein said yeast strain deficient in vacuolar proteases A and B is ABYSD-11

(DSM 4322) and said yeast strain which is auxotrophic or chemically-sensitive is TCY2824-1A (DSM 4317).

7. Process of claim 5 wherein said recombinant DNA molecule further comprises one or more genes which complement the auxotrophy or chemical sensitivity of said auxotrophic or chemically sensitive strain.

8. Process of claim 1 or 5, wherein said recombinant DNA molecule is a plasmid, an integration vector or an integrating DNA fragment.

9. Process according to claim 1 or 5, wherein said recombinant DNA molecule is a yeast plasmid which occurs in a high copy number in a yeast cell.

10. Process according to claim 6 wherein said protein is α-glucosidase.

11. The process of claim 5 further comprising a yeast strain deficient in vacuolar protease A, vacuolar protease B, cytoplasmic protease D and vacuolar carboxypeptidases Y and S.

* * * * *